US012766091B2

(12) United States Patent
Khan et al.

(10) Patent No.: US 12,766,091 B2
(45) Date of Patent: Oct. 20, 2026

(54) COSMETIC USE OF AN OILY EXTRACT FROM DISTILLATION RESIDUE OF IMMORTELLE AS A SKIN BRIGHTENING AGENT

(71) Applicant: LABORATOIRES M&L, Manosque (FR)

(72) Inventors: Cédric Khan, Pierrevert (FR); Valérie Cenizo, Meyrargues (FR); Virginie Rouquet, Manosque (FR)

(73) Assignee: LABORATOIRES M&L, Manosque (FR)

( * ) Notice: Subject to any disclaimer, the term of this patent is extended or adjusted under 35 U.S.C. 154(b) by 275 days.

(21) Appl. No.: 18/566,124

(22) PCT Filed: May 13, 2022

(86) PCT No.: PCT/FR2022/050914
§ 371 (c)(1),
(2) Date: Dec. 1, 2023

(87) PCT Pub. No.: WO2022/254116
PCT Pub. Date: Dec. 8, 2022

(65) Prior Publication Data

US 2024/0277603 A1 Aug. 22, 2024

(30) Foreign Application Priority Data

Jun. 3, 2021 (FR) ...................................... 2105840

(51) Int. Cl.

| | |
|---|---|
| ***A61K 36/00*** | (2006.01) |
| ***A61K 8/36*** | (2006.01) |
| ***A61K 8/37*** | (2006.01) |
| ***A61K 8/63*** | (2006.01) |
| ***A61K 8/9789*** | (2017.01) |
| ***A61Q 19/02*** | (2006.01) |

(52) U.S. Cl.
CPC ............ *A61K 8/9789* (2017.08); *A61K 8/361* (2013.01); *A61K 8/37* (2013.01); *A61K 8/63* (2013.01); *A61Q 19/02* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 9,956,151 | B2 | 5/2018 | Santhanam et al. | |
| 10,166,412 | B2 | 1/2019 | Dutta et al. | |
| 2020/0113959 | A1 * | 4/2020 | Lemaire ............... | A61K 8/9789 |

FOREIGN PATENT DOCUMENTS

| | | | |
|---|---|---|---|
| FR | 3 079 144 | 3/2018 | |
| WO | WO-2017077232 A1 * | 5/2017 | ........... A61K 8/9789 |
| WO | WO-2019180368 A1 * | 9/2019 | ............. A61Q 19/00 |

OTHER PUBLICATIONS

Acimovic et al. (2024) Natural Products Comm. vol. 19(9): 1-16. (Year: 2024).*
Granger et al. (2020) Dermatol. Ther. (Heidelb.) 10: 1315-1329. (Year: 2020).*
Raskin et al. (2004) Current Pharmaceutical Design 10, 3419-3429. (Year: 2004).*
Revilla et al. (1998) J. Agric. Food Chem. 46: 4592-4597. (Year: 1998).*
Written Opinion in International Application No. PCT/FR2022/050914, Sep. 6, 2022, pp. 1-7.

* cited by examiner

*Primary Examiner* — Russell G Fiebig
(74) *Attorney, Agent, or Firm* — SALIWANCHIK, LLOYD & EISENSCHENK

(57) ABSTRACT

The present invention relates to the cosmetic use of an oily extract from solid residue of immortelle as a brightening agent for the complexion. The invention also relates to a cosmetic composition comprising, in a physiologically acceptable medium, an oily extract of immortelle draff and hexylresorcinol, as well as to the uses of this composition.

14 Claims, 2 Drawing Sheets

COSMETIC USE OF AN OILY EXTRACT FROM DISTILLATION RESIDUE OF IMMORTELLE AS A SKIN BRIGHTENING AGENT

CROSS-REFERENCE TO RELATED APPLICATION

This application is the U.S. national stage application of International Patent Application No. PCT/FR2022/050914, filed May 13, 2022.

FIELD OF THE INVENTION

The present invention relates to the cosmetic use of an oily extract of immortelle distillation residue as a skin-lightening agent. The invention also relates to a cosmetic composition comprising, in a physiologically acceptable medium, an oily extract of immortelle distillation residue and hexylresorcinol, and also to the uses of this composition.

BACKGROUND OF THE INVENTION

The mechanism of skin pigmentation is a complex process involving the production of melanin by the melanocytes, which are specialized cells located in the basal layer of the epidermis. Schematically, this mechanism involves the following main steps: Tyrosine→Dopa→Dopaquinone→Dopachrome→Melanin, catalyzed by tyrosinase, the key enzyme involved in this sequence of reactions.

Skin color is mainly determined by the type and concentration of melanin produced by the melanocytes. Melanocytes can be activated by internal or external stimuli to produce melanin in specialized lysosome-like organelles called melanosomes. After maturation, perinuclear melanosomes are transported along microtubules and the actin cytoskeleton to the periphery of the melanocyte dendrites. The melanosomes, which contain melanin, are then transferred to adjacent keratinocytes.

Impairment of any step in this complex process can lead to skin pigmentation disorders. In particular, an increase in the number of active melanocytes, and/or an increase in melanin production, and/or an increase in the transfer of melanosomes from melanocytes to keratinocytes may lead to hyperpigmentation of the skin.

Thus, environmental, genetic and/or hormonal factors can modulate the amount, type and distribution of melanin in the skin and/or hair, with significant cosmetic and psychological consequences. Darker and/or more colored spots may thus appear on the skin and more especially on the hands of certain people in the sun. Other types of regional hyperpigmentation due to melanocyte hyperactivity are idiopathic melasma, occurring during pregnancy ("pregnancy mask" or chloasma) or estroprogestogenic contraception. Conversely, skin hypopigmentation may be observed in cases of exposure of scars to the sun, or in certain leukodermias such as vitiligo. In these cases, if it is not possible to repigment the damaged skin, the remaining areas of normal skin are depigmented to give the skin as a whole a uniform white hue.

The use of harmless topical depigmenting substances with good efficacy is particularly sought in order to treat all these hyperpigmentations. A substance is recognized as being bleaching or depigmenting if it acts directly on the vitality of the epidermal melanocytes where melanogenesis takes place, and/or if it interferes with one of the steps of melanin biosynthesis, either by inhibiting one of the enzymes involved in melanogenesis, in particular tyrosinase, or by intercalating as a structural analog of one of the chemical compounds in the melanin synthesis chain, which chain can then be blocked, thus ensuring depigmentation and hence skin lightening. Various cosmetic active agents, such as vitamin C and derivatives thereof, arbutin, azelaic acid, glycolic acid, n-butylresorcinol (or rucinol), hexylresorcinol, and also glutathione and derivatives thereof, are currently used for treating these hyperpigmentation problems. These compounds have different modes of action, including inhibition of tyrosinase activity, reduction of the amount of melanin formed, and even stimulation of melanin elimination in keratinocytes. Some of these compounds may, however, cause side effects such as burns, erythema and skin dryness.

There thus remains a need for a novel human skin bleaching agent which is as effective as those already known, but which does not have their drawbacks, i.e. which is non-irritant, non-toxic and/or non-allergenic to the skin.

In this context, it has already been proposed to use various immortelle extracts as bleaching agents, notably an extract obtained by extraction, using a solvent such as ethanol, of the aerial parts of *Helichrysum gymnocephalum* (DC) Humbert. This extract is characterized by the presence of monoterpene derivatives of chalcone or dihydrochalcone, in particular gymnochalcone (FR2970416). Mention may also be made of WO 2007/015232, which suggests the use of an (undefined) extract of *Helichrysum arenarium* in a process for eliminating scars and skin pigmentation, and of CN111973544, which discloses the depigmenting effect of a water-glycol extract of *Helichrysum bracteatum*. Bleaching properties have also been attributed to *Helichrysum angustifolium* essential oil (CN108670926). Moreover, a combination of several different immortelle extracts has been suggested for its antiaging properties, and also its ability to reduce pigment spots (FR3003167). Finally, patent application WO 2019/086602 suggests that a subcritical water extract of the flowering tops of *Helichrysum italicum*, containing caffeoylquinic acid, may have depigmenting properties and be used as an anti-blemish cosmetic active agent.

The Applicant has now demonstrated, quite surprisingly, that another immortelle extract, already known for its properties of stimulating keratinocyte differentiation and its ability to restore the skin barrier (WO 2019/180368), shows good depigmenting activity, even at low concentrations, while at the same time being well tolerated.

SUMMARY OF THE INVENTION

The subject of the invention is, precisely, the cosmetic use of an oily extract of immortelle distillation residue of the *Helichrysum italicum* species, applied topically to the skin, as an agent for bleaching the skin and/or lightening the complexion and/or for homogenizing skin color and/or reducing or preventing the appearance of pigment spots.

Another subject of the invention is an agent for bleaching the skin and/or lightening the complexion and/or for homogenizing skin color and/or reducing or preventing the appearance of pigment spots, consisting of an oily extract of immortelle distillation residue of the *Helichrysum italicum* species.

Another subject of the invention relates to a cosmetic composition comprising, in a physiologically acceptable medium, from 0.01% to 1% by weight of an oily extract of immortelle distillation residue as defined above, and from 0.001% to 5% by weight of hexylresorcinol, relative to the total weight of the composition.

A subject of the invention is also the cosmetic use of the abovementioned cosmetic composition for bleaching the skin and/or lightening the complexion and/or for homogenizing the skin color and/or reducing or preventing the appearance of pigment spots, comprising the topical application of this composition to the skin.

A subject of the invention is also a cosmetic process for bleaching the skin and/or lightening the complexion and/or for homogenizing the skin color and/or reducing or preventing the appearance of pigment spots, comprising the topical application to the skin of the abovementioned composition.

DETAILED DESCRIPTION

The present invention uses an oily extract of immortelle distillation residue of the *Helichrysum italicum* species, preferentially of Corsican origin.

The term "distillation residue" means the solid residue remaining after hydrodistillation or steam distillation of any part of the immortelle plant and separation of the essential oil and hydrosol produced. The immortelle distillation residue used according to the invention are thus obtained according to a process comprising a step of hydrodistillation or steam distillation of all or part of the plant, preferably the aerial parts of the plant, in particular its flowers or flowering tops, followed by a step of recovery of the distillation or steam distillation residue.

The oily extract from the distillation residue may then be obtained via any process for extracting oil from distillation residue, and more particularly by extracting the distillation residue using a supercritical fluid, such as carbon dioxide, nitric oxide, dimethyl ether, propane, ethylene or methanol, without this list being limitative. Carbon dioxide in the supercritical state may thus be used. A person skilled in the art will know how to adjust the extraction parameters, notably temperature, pressure and fluid flow rate, as a function of the desired extraction speed and yield. For example, extraction using supercritical $CO_2$ may be performed at a pressure of 250 to 300 bar and a temperature of 40 to 80° C., preferably 50 to 70° C. After extraction, the supercritical fluid is returned to the gaseous state by decompression and generally recycled. The plant extract thus obtained is then advantageously subjected to a molecular distillation step, for example at a temperature of 180 to 250° C., preferably 200 to 220° C., so as to concentrate the unsaponifiable matter present in the extract. Prior to this molecular distillation step, the plant extract may optionally be diluted in an oily solvent, notably based on a plant oil such as sunflower oil. This oily solvent is removed during the molecular distillation step.

According to a preferred embodiment, the oily extract of immortelle distillation residue used according to the invention is obtained according to a process comprising a step of extracting the distillation residue with a supercritical fluid, preferably carbon dioxide in the supercritical state, optionally followed by a molecular distillation step.

A distillate is thus obtained notably containing from 30% to 50% by weight, more particularly from 35% to 45% by weight, of unsaponifiable matter and from 1% to 10% by weight, more particularly from 3% to 7% by weight, of sterols, essentially beta-sitosterol.

The extract obtained using the supercritical fluid or the distillate resulting from the molecular distillation step may optionally be diluted in an oily solvent, to a concentration of 1% to 10% by weight, for example, notably 3% to 5% by weight, so as to facilitate handling. Any oily solvent suitable for cosmetic use may be used for this purpose, notably fatty acid triglycerides such as caprylic/capric triglyceride. The Applicant characterized the oily extract of immortelle distillation residue by gas chromatography coupled to mass spectrometry. It was thus demonstrated that the oily extract of immortelle distillation residue contains less than 10% volatile fraction, as determined by gas chromatography.

It was also shown that the oily extract of immortelle distillation residue used according to the invention differed, in terms of its composition, from an extract obtained by supercritical $CO_2$ of immortelle flowering tops in that it contained substantially no (i.e. less than 10% by weight, or even less than 5% by weight or even less than 2% by weight), if at all any, of palmitoleic acid, linalool, nerol, 2-decenal, 2-tridecanone, heptadecane, 8-heptadecene, isobutyric acid, isovaleric acid, hexadecenol, lauric acid, pentadecanoic acid, decanoic acid and isostearic acid. More generally, this extract contains no saturated fatty acids containing more than 10 carbon atoms. Conversely, the oily extract of immortelle distillation residue used according to the invention contains constituents that have not been identified in an extract obtained by supercritical $CO_2$ of immortelle flowering tops, namely 2(Z)-decenoic acid and 4(Z)-decenoic acid.

In addition, compared with immortelle essential oil, the oily extract of immortelle distillation residue used according to the invention contains sterols, essentially beta-sitosterol, linear carboxylic acids, $C_7$-$C_{10}$ linear, saturated or unsaturated carboxylic acids (in particular heptanoic, octenoic and decenoic acids), benzoic acid and ethyl esters of $C_8$-$C_{18}$ linear, saturated or unsaturated fatty acids (in particular caprylate, caprate and linoleate).

It also differs from an immortelle oily extract obtained by extraction using sunflower oil in that it does not contain any limonene and contains fatty acids and/or ethyl esters thereof (heptanoic, 2-octenoic, 4-octenoic, nonanoic, 2-decenoic, 4-decenoic, linoleic acids) and benzoic acid which are not present in the abovementioned oily extract.

Finally, the oily extract of immortelle distillation residue used according to the invention is low in polyphenols and notably is free of dicaffeoylquinic acid and chalcones.

The oily extract of immortelle distillation residue advantageously represents from 0.01% to 1% relative to the total weight of the composition according to the invention.

The oily extract of immortelle distillation residue according to the invention is included in a cosmetic composition which contains a physiologically acceptable medium, in particular a cosmetically acceptable medium, i.e. one which does not give rise to any tingling or redness incompatible with cosmetic use. This medium preferably contains an aqueous phase and/or a fatty phase. Preferably, the composition is in the form of an emulsion, notably of the oil-in-water or water-in-oil type, or an anhydrous oily composition. The term "anhydrous composition" refers to a composition containing less than 5% by weight of water, preferably less than 2% by weight of water, or even no water at all.

When it is present, the aqueous phase contains water and optionally at least one constituent chosen from polyols and aqueous gelling agents. Water advantageously represents from 40% to 80%, for example from 50% to 70%, of the total weight of the composition. The polyol may notably be chosen from glycerol, propylene glycol, butylene glycol, pentylene glycol and mixtures thereof, and may represent from 5% to 30%, preferably from 15% to 25%, of the total weight of the composition.

The term "aqueous gelling agent" denotes a polymeric compound that is capable of immobilizing water molecules by becoming hydrated and thus of increasing the viscosity of the aqueous phase. Such a gelling agent may be chosen from: polysaccharides, such as: cellulose and derivatives thereof, modified starches, carrageenan, agar agar, xanthan gum and plant gums such as guar gum or locust bean gum; synthetic polymers and notably optionally crosslinked sodium acrylate homopolymers, and also acrylic copolymers, in particular sodium acrylate and/or alkyl (meth) acrylate and/or hydroxyalkyl (meth)acrylate and/or (polyethoxy)alkyl (meth)acrylate copolymers, optionally with at least one other monomer, advantageously 2-acrylamido-2-methylpropanesulfonic acid (AMPS), these copolymers being optionally crosslinked; and mixtures thereof.

For its part, when it is present, the fatty phase may comprise one or more volatile and/or nonvolatile oils. Examples of volatile oils are branched alkanes, such as isododecane, and linear $C_{10}$-$C_{13}$ alkanes. Nonvolatile oils that may notably be mentioned include:

- acid and monoalcohol esters chosen from: mono- and polyesters of saturated linear C2-C10 (preferably C6-C10) acids and of saturated linear C10-C18 (preferably C10-C14) monoalcohols, mono- and polyesters of saturated linear C10-C20 acids and of branched or unsaturated C3-C20 (preferably C3-C10) monoalcohols; mono- and polyesters of branched or unsaturated C5-C20 acids and of branched or unsaturated C5-C20 monoalcohols; mono- and polyesters of branched or unsaturated C5-C20 acids and of linear C2-C4 monoalcohols;
- triglycerides of C6-C12 fatty acids, such as caprylic and capric acid triglycerides and triheptanoin;
- branched and/or unsaturated C10-C20 fatty acids (such as oleic acid and linoleic acid);
- branched and/or unsaturated C10-C20 fatty alcohols (such as octyldodecanol and oleyl alcohol);
- hydrocarbons such as squalane (C30), notably plant squalane extracted from olive oil, and hemisqualane (C15);
- dialkyl carbonates, such as dicaprylyl carbonate and diethylhexyl carbonate;
- dialkyl ethers, such as dicaprylyl ether; and
- mixtures thereof.

Mention may also be made of plant oils containing one or more of the abovementioned constituents.

As esters of acids and monoalcohols, mention may notably be made of monoesters such as the cocoyl caprate/caprylate mixture, ethyl macadamiate, shea butter ethyl ester, isostearyl isostearate, isononyl isononanoate, ethylhexyl isononanoate, hexyl neopentanoate, ethylhexyl neopentanoate, isostearyl neopentanoate, isodecyl neopentanoate, isopropyl myristate, octyldodecyl myristate, isopropyl palmitate, ethylhexyl palmitate, hexyl laurate, isoamyl laurate, cetostearyl nonanoate, propylheptyl caprylate and mixtures thereof. Other esters that may be used include diesters of acids and of monoalcohols, such as diisopropyl adipate, diethylhexyl adipate, diisopropyl sebacate and diisoamyl sebacate.

Examples of plant oils are notably wheat germ oil, sunflower oil, argan oil, hibiscus oil, coriander oil, grapeseed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, lavender oil, borage oil, millet oil, barley oil, *quinoa* oil, rye oil, safflower oil, candlenut oil, passionflower oil, rose hip oil, *Echium* oil, camelina oil and *camellia* oil.

The fatty phase may also comprise at least one fatty-phase structuring agent. The term "fatty-phase structuring agent" means a compound that is capable of thickening the oils contained in the composition, chosen notably from waxes, fatty-phase gelling agents and pasty fatty substances, and also mixtures thereof.

According to a preferred embodiment, this composition also contains at least one depigmenting active agent other than the oily extract of immortelle distillation residue, which may notably be chosen from: plant extracts, in particular licorice extract; vitamin C and derivatives thereof, in particular ascorbic acid, ascorbyl glucoside, ascorbic acid ethyl ether, ascorbyl tetraisopalmitate and magnesium ascorbyl phosphate; arbutin; ferulic acid; kojic acid; resorcinol and derivatives thereof, such as hexylresorcinol and 4-(1-phenylethyl)-1,3-benzenediol, notably sold under the trade name Symwhite 377® by the company Symrise; salicylic acid, salts thereof and esters thereof, meadowsweet and *Iris florentina* extracts; dipotassium glycyrrhizinate; tranexamic acid; ellagic acid; nicotinic acid derivatives such as niacinamide; extract of kiwi fruit (*Actinidia chinensis*) sold by Gattefossé; extract of peony root (*Paeonia suffruticosa*) sold by Ichimaru Pharcos under the trade name Botanpi® Liquid; lipoamino acid (phenylalanine modified with undecylenoic acid) sold under the trade name Sepiwhite® by SEPPIC; *Helichrysum italicum* essential oil; and mixtures thereof.

In a preferred embodiment of the invention, the cosmetic composition contains, in a physiologically acceptable medium, from 0.01% to 1% by weight, preferably from 0.05% to 1% by weight, and more preferentially from 0.05% to 0.3% by weight, of an oily extract of immortelle distillation residue as defined previously and from 0.001% to 5% by weight of hexylresorcinol, relative to the total weight of the composition.

Hexylresorcinol, or 4-hexyl-1,3-phenylenediol, means the compound of chemical structure:

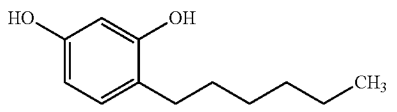

Hexylresorcinol is known for its depigmenting and skin-protecting properties. Preferably, the hexylresorcinol introduced into the cosmetic composition of the invention is purified and contains almost no resorcinol (the latter compound being unstable and having an irritant effect on the skin). For this purpose, it is possible to use the product obtained via the process described in the Sythéon patent EP 2 152 685, or directly the commercial product Synovea® HR, which is known to contain over 99.5% hexylresorcinol, to inhibit melanin production in vitro (Funasaka A. H. et al., J. Lipid Res. 1999) and to have bleaching activity on the skin of human volunteers (EP 2 152 685).

As emerges from the examples hereinbelow, the oily extract of immortelle distillation residue according to the invention has been shown to potentiate the depigmenting effect of hexylresorcinol.

As a variant or in addition, this cosmetic composition may comprise at least one active agent chosen from: free-radical scavengers, moisturizers, agents for stimulating the differentiation and/or proliferation of keratinocytes and/or fibroblasts; agents for stimulating the synthesis of glycosaminoglycans and/or collagen and/or dermoepidermal anchoring fibrils and/or elastic fibers; agents for preventing the degradation of collagen and/or glycosaminoglycans and/or dermoepidermal anchoring fibrils and/or elastic fibers; antiglycation agents; and mixtures thereof.

Examples of such antiaging active agents are notably: ascorbic acid, and salts, ethers and esters thereof, notably ascorbyl glucoside; adenosine; ribose; honey extracts; proteins and glycoproteins, notably extracted from sweet almond; hydrolyzed plant proteins, notably derived from rice, hibiscus seeds or lupin; polypeptides and pseudodipeptides, such as carcinine hydrochloride, palmitoyl pentapeptide-4 (Pal-Lys-Thr-Thr-Lys-Ser) and palmitoyl tripeptide-38 sold notably by Sederma under the trade names Matrixyl® 3000 and Matrixyl® Synthe'6, respectively, and palmitoyl tripeptide-8 sold by the company Lucas Meyer under the trade name Nutrazen®, pentapeptide-18 sold by the company Lipotec under the trade name Leuphasyl® Solution, sh-decapeptide-9 sold by the company Sandream under the trade name Neoendorphin® and palmitoyl hexapeptide-52 sold by the company Infinitec under the trade name X50 Myocept® Powder; silanes such as methylsilanol mannuronate; arabinoxylans, extracted in particular from rye flour and galactoarabinans, derived notably from larch; hyaluronic acid and salts thereof, polyphenols, extracted in particular from *mimosa*; α-hydroxy acids, including those extracted from lemon and those extracted from hibiscus, sold under the trade name Hibiscus Acids® by Naturex; extracts (generally aqueous) of plants such as water clover, wild pansy, horsetail, mafane (*Acmella oleracea*), donkey thistle (*Onopordum acanthium*), yarrow (*Achillea millefolium*, notably contained in the product Neurobiox® from the company BASF), *embelia* (*Embelia concinna*, as sold by the company SEPPIC), prickly pear (*Opuntia ficus* indica, sold notably by Mibelle AG Biochemistry under the trade name AquaCacteen@), sage (*Salvia officinalis*, sold notably by Provital Group), *Vitex negundo* (sold notably by Laboratoires Expanscience under the trade name Neurovity®), chestnut, *papaya*, argan, oat, sunflower, daisy, peony or dill; aqueous seaweed extracts, notably of coralline, slender-beaded coral weed, *Ungaria pinnatifada, Alaria esculenta* or *Nannochlorosis oculata*; essential oils, notably of myrtle; zinc and/or copper gluconates; and mixtures thereof.

The composition according to the invention may also contain various constituents which may be dispersed in the fatty phase and/or in the aqueous phase, provided these are compatible with topical application to the skin.

It may thus contain at least one generally nonionic oil-in-water or water-in-oil emulsifier, such as polyoxyethylene esters, optionally polyethoxylated sorbitan esters, optionally polyethoxylated fatty acid esters of glycerol, fatty alcohol ethers of sugars, such as alkyl glucosides, and mixtures thereof. The emulsifiers may represent from 2% to 10% and preferably from 4% to 6% of the total weight of the composition.

The composition according to the invention may also comprise one or more pulverulent fillers, which are advantageously in the form of porous or hollow, preferably porous, microparticles. These microparticles are in principle substantially spherical. These fillers may notably be chosen from:

- organic fillers such as: powders of polysaccharides and in particular native starch, modified starch or cellulose; powders of acrylic polymers such as poly(methyl methacrylate), polyamides or polyolefins; powders of dried algae such as *Corallina officinalis;*
- mineral fillers such as silica, clays, perlite and talc;
- and mixtures thereof.

Silica is preferred for use as mineral filler.

These fillers may represent from 1% to 5% by weight, relative to the total weight of the composition.

The composition according to the invention may also comprise additives notably chosen from organic and/or inorganic photoprotective agents, which are active in blue light and/or UVA and/or UVB; polysaccharide-based film-forming polymers that are capable of forming an antipollution protective film, such as the products sold by Solabia under the trade names Pollustop® and Solashield®; fragrances; antioxidants; sequestrants; pH adjusters; preserving agents; pigments; colorants; and mixtures thereof.

This composition may be in any form that is suitable for topical application to the skin, notably in the form of a milk, cream, fluid, lotion, gel, paste, oil or film. It is generally a leave-on composition and in particular a skincare composition.

As a variant, the composition according to the invention may be a rinse-off composition used for skincare, in particular for the face and possibly the body. In this case, it may be used, for example, as a mask or as an exfoliating paste.

The composition according to the invention may be applied to the skin of people with skin color inhomogeneity mediated by environmental factors, notably pigment spots, chloasma and/or pigmentation defects due to scars or acne marks. It is generally applied to at least one area of the body concerned and more particularly to the skin of the face, neckline, neck, arms, hands and/or legs, with a view to lightening these areas and/or unifying the skin color. This composition may be applied once or several times a day, for example morning and/or evening.

In any case, the oily extract of immortelle distillation residue is applied to the skin in an amount sufficient to inhibit melanogenesis. For example, an amount of 0.5 to 5 $mg/cm^2$ of cosmetic composition containing 0.01% to 1% by weight of oily extract of immortelle distillation residue according to the invention may be applied daily to the skin area concerned.

FIGURES

EXAMPLES

Figure 1:
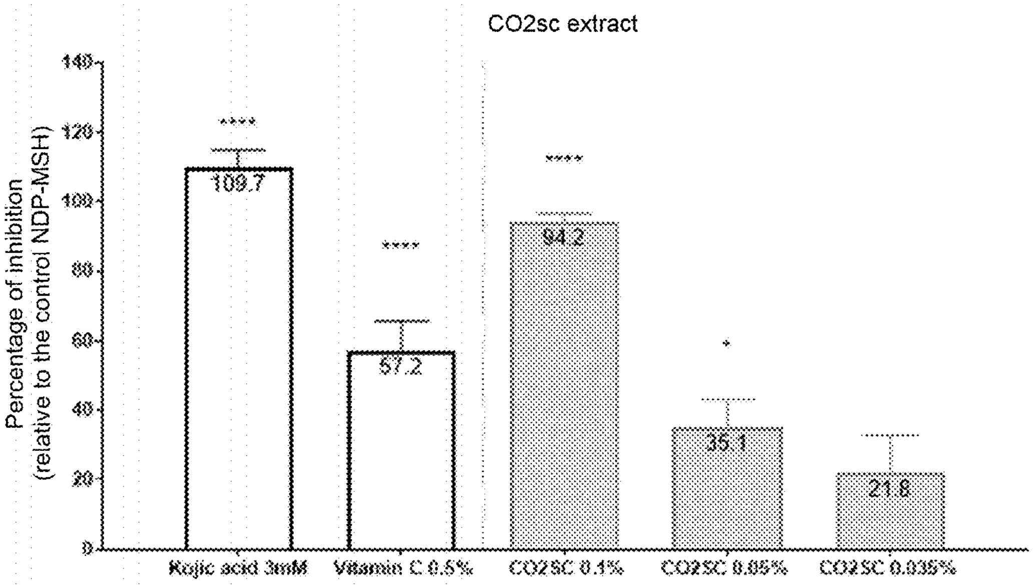
FIG. 1 illustrates the effect of the extract according to the invention on the inhibition of melanin production by mouse B16 melanocytes, in comparison with two positive controls.

The invention will be understood more clearly in the light of the following examples, which are given purely by way of illustration and are not intended to limit the scope of the invention, defined by the appended claims.

Example 1: Preparation and Characterization of the Extract—Comparison with an Oily Extract of Flowering Tops 1.1—Preparation of the Extracts An essential oil and a hydrosol were produced by hydrodistillation of the flowering tops of *Helichrysum italicum*, then the hydrodistillation residue (distillation residue) was isolated and extracted using supercritical $CO_2$ at a temperature of 60° C. and a pressure of 285 bar. The unsaponifiable matter thus obtained was diluted in sunflower oil, and then subjected to a step of molecular distillation at 200° C. and the resulting distillate was standardized by diluting it to 3-5% by weight in caprylic/capric triglycerides.

The polyphenol composition of this extract was compared with that of an oily extract of *Helichrysum italicum* obtained as follows: 9% by weight of dried and ground plant powder (flowering tops) was mixed with 91% of an ultrasound-deodorized sunflower oil, in a container cooled to 10° C. Extraction was performed for 30 min, under ultrasound, with stirring at 500 rpm. Extraction was continued by microwave under a nitrogen flow of 0.4 L/min. The solid and liquid oily phases obtained were separated by decantation, then the oily phase was filtered and stored under an inert atmosphere, protected from light.

1.2—Characterization of the Polyphenols

Materials

- Ultra high performance liquid chromatograph (Agilent Technologies, USA) USA).
- 1290 series automatic injector.
- 1260 series diode array detector (DAD).
- Mass spectrometer: Esquire 6000 (Brüker Daltonics, Bremen) equipped with an electrospray ionization (ESI) source.

Preparation of the Samples

The extract according to the invention was prepared by dissolving 2 g of distillation residue extract in 1 mL of hexane. This oily solution was extracted three times with 2 mL of $MeOH/H_2O$ mixture (60/40). The $MeOH/H_2O$ phases were then pooled and diluted %2 in $MeOH/H_2O$ mixture (60/40).

Analysis Method

The solutions obtained after dilution/extraction were filtered through a PTFE filter (0.45 μm) and then injected (1 μL) onto an Agilent C18 column (2.1 mm×100 mm; 1.8 μm) at a temperature maintained at 25° C. and a flow rate of 0.4 mL/min. The solvents used were: A=$H_2O$/HCOOH (0.1%) and B=ACN/HCOOH (0.1%). The polyphenol elution gradient was as follows:

TABLE 1

| Time (min) | % Solvent B |
|---|---|
| 0 | 5 |
| 2 | 18.3 |
| 6 | 29 |
| 6.5 | 31.7 |
| 9.5 | 38.3 |
| 11.5 | 71 |
| 15 | 95 |
| 16 | 100 |
| 17 | 100 |
| 17.2 | 5 |
| 20.2 | 5 |

On leaving the diode array detector, the eluent was injected into the mass spectrometer. The analyses were performed in negative or positive mode.

LC-MS spectra were acquired over the entire mass range (mz) from 100 to 1400. All the data were then collected and processed using the Hystar version 3.0 software.

Results

TABLE 2

| Compound | Residue extract |
|---|---|
| Chlorogenic acid isomer | n.d. |
| Chlorogenic acid | n.d. |
| Chlorogenic acid isomer | n.d. |
| Dicaffeoylglucaric acid | n.d. |
| Caffeic acid | n.d. |
| Dicaffeoylglucaric acid | n.d. |
| Quercetagetin O-hexoside | n.d. |
| Flavonoid O-hexoside | n.d. |
| Dicaffeoylquinic acid | n.d. |
| Dicaffeoylquinic acid | n.d. |
| Dicaffeoylquinic acid | n.d. |
| Dicaffeoylquinic acid | n.d. |
| Dicaffeoylquinic acid | n.d. |
| Quercetin O-hexoside-O-rhamnoside | n.d. |
| Arzanol | 37.7 ± 1.3 |
| Methylarzanol | 2.4 ± 0.3 |
| Dimethylarzanol | n.d. |
| 12-Hydroxytremetone | Presence |
| Gnaphaliol | Presence |

n.d: not detected;

<LQ: detected but below the limit of quantification 1.3—Characterization of the Chalcones The presence of four chalcones (linderatin, linderachalcone, methyl-linderatin, gymnochalcone) in the distillation residue extract described above was evaluated using a 2D NMR method with $^1H/^{13}C$ HSQC spectrum.

Materials and method: An aliquot of the distillation residue extract (15 mg) was dissolved in 700 μL of DMSO-d6 so as to be analyzed by 2D NMR at 298 Kelvin. 2D NMR analysis was performed using a Bruker Avance AVIII-600 spectrometer equipped with the Cryoprobe® NMR probe. The NMR values obtained were compared with those calculated using the ACD Labs software.

Result: no chalcones were detected in the sample.

1.4—Characterization of the Other Constituents

In parallel, the presence of various organic compounds was evaluated in the above two extracts, and also in an extract obtained in a similar manner to the extract according to the invention, but using a process performed on immortelle flowering tops and not on their hydrodistillation residue.

Materials

- Trace GC Ultra gas chromatograph (ThermoElectron SAS).
- Mass spectrometer: El LT Large T ISQ Mass Spectrometer (ThermoElectron SAS) used in El mode.

Preparation of the Samples

The samples were prepared by diluting 0.3 g of extract in 6 mL of isooctane. 0.6 mL of methanolic potassium hydroxide was added and the mixture vortexed for 30 s. 1 g of $NaHSO_4$ was added and the mixture vortexed for 30 sec.

The mixture was then allowed to separate by settling.

The upper part of the supernatant was taken up for chromatographic analysis.

Analysis Method

The samples were analyzed under the following conditions:

- TR WAX 60 m×0.25 μm×0.25 mm polar chromatography column
- $H_2$ flow rate: 1 mL/min
- Oven program: 50° C. (2 min) then 10° C./min up to 250° C. (18 min)
- Split ratio: 100
- Injection volume: 1 μL
- Injector temperature: 250° C.

Mass range: 50-650 amu

Results

It was notably observed that the extract of immortelle distillation residue according to the invention differs from the oily extract of flowering tops in that it does not contain limonene, contains significantly more β-eudesmol and contains fatty acids and/or ethyl esters thereof (heptanoic, 2-octenoic, 4-octenoic, nonanoic, 2-decenoic, 4-decenoic and linoleic acids) and benzoic acid, which are not present in the oily extract of immortelle flowering tops.

In addition, the distillation residue extract according to the invention differs notably from the supercritical $CO_2$ extract of flowering tops in that it contains no saturated fatty acids containing more than 10 carbon atoms, and in that it contains far fewer, if any, terpenoids (notably monoterpenes and sesquiterpenes), in particular, it is free of nerol and linalool, and contains far fewer, if any, heavy alkanes (containing more than 16 carbon atoms), and is free of palmitoleic, isobutyric and isovaleric acids, 2-decenal and hexadecenol. Moreover, the distillation residue extract according to the invention contains characteristic molecules not present in the supercritical $CO_2$ extract of flowering tops, namely (2)-(Z)-decenoic and 4-(Z)-decenoic acids.

Example 2: Effect of the Immortelle Distillation Residue Extract According to the Invention on Melanogenesis The immortelle distillation residue extract and the oily extract of flowering tops described in Example 1 were tested to evaluate their ability to inhibit melanin production.

2.1—Materials & Method

Melanocytes (mouse line B16) were seeded in 96-well plates at 2000 cells per well in phenol red-free DMEM medium containing 10% fetal calf serum, 2 mM glutamine, 1 mM sodium pyruvate and 100 μg/ml normocin. The following day, the cells were treated with 0.1 μM of NDP-MSH to induce pigmentation. Under the test conditions, in the presence of NDP-MSH, kojic acid at 3 mM and vitamin C (ascorbyl glucoside) at 0.5% were used as positive controls for pigmentation inhibition, and the extracts to be evaluated were tested at several concentrations. All the conditions were tested in triplicate. The cells were incubated at 37° C., 5% $CO_2$ for 72 h in the presence of the extracts and positive controls. The cell viability was then evaluated using the XTT method, and only the non-cytotoxic conditions (whose viability was greater than 85% of that of the untreated control) were analyzed for melanin amount.

For the melanin assay, the medium in each well was aspirated and the cells lyzed by adding 50 μl of 1M NaOH to the cell lawn. The plates were shaken for 30 minutes at room temperature, and the lyzate was then transferred to glass flasks and incubated overnight at 95° C. After incubation, the lyzates were centrifuged at 2000 rpm to remove the cell debris. The absorbance of the supernatant was read at 405 nm, reflecting the amount of melanin in each well, and the average of the three replicates was determined for each condition. A well of cells not treated with NDP-MSH was used as a control, and its OD value subtracted from all the OD values of the other wells. The percentage of melanin inhibition was then calculated according to the formula:

$$100-((\text{melanin amount in test condition}/\text{melanin amount in untreated control})\times 100).$$

The significance of the results was evaluated using a one-way Anova test (for the distillation residue extract and the oily extract of flowering tops) or Student's t test (for kojic acid and vitamin C).

2.2—Results

Figure 2:
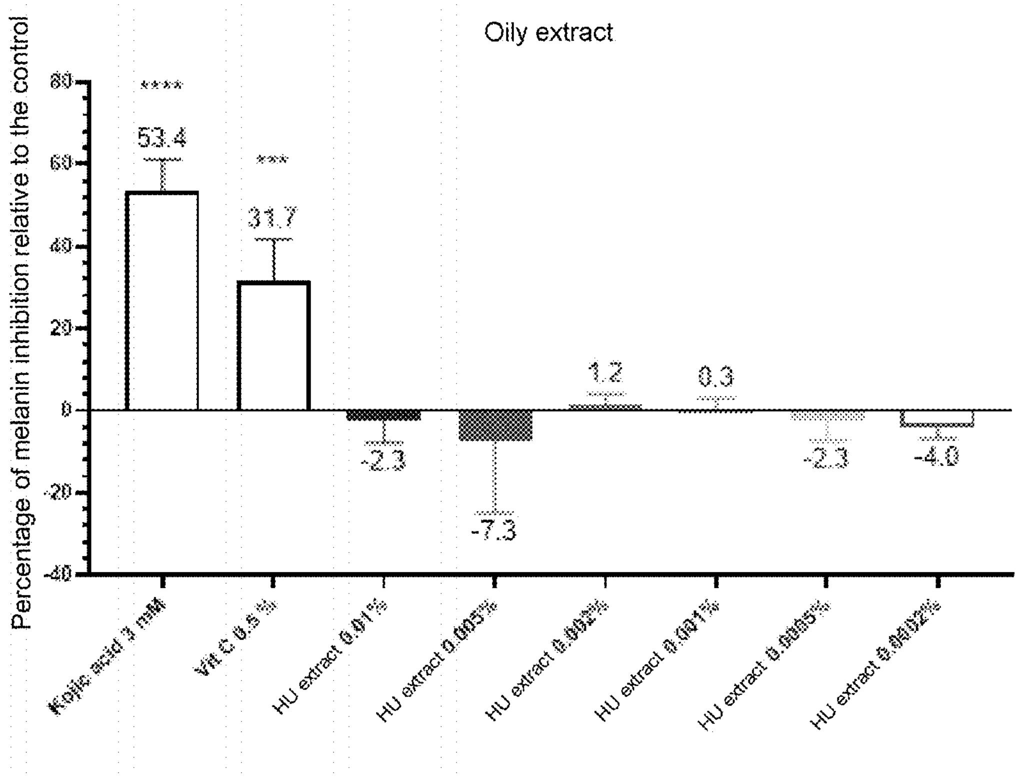
FIG. 2 illustrates the effect of an oily extract of *Helichrysum italicum* on the inhibition of melanin production by mouse B16 melanocytes, in comparison with two positive controls.

As shown in FIGS. 1 and 2, the test was validated by demonstrating the efficacy of kojic acid and vitamin C (*$p<0.001$; **$p<0.0001$).

FIG. 1 also shows that the immortelle distillation residue extract according to the invention significantly inhibits melanocyte pigmentation in a dose-dependent manner at and above a concentration of 0.05% (****$p<0.0001$ at 0.1%; *$p<0.05$ at 0.05%). At a concentration of 0.1%, the distillation residue extract according to the invention has much higher efficacy than the highest concentration of vitamin C, which constitutes the bleaching active agent conventionally used in cosmetics. Its efficacy is close to that of kojic acid, which is a benchmark depigmenting agent, but is known to entail severe risks of allergy and irritation.

This example thus demonstrates that the immortelle distillation residue extract according to the invention constitutes a cosmetic active agent of choice for skin lightening.

In comparison, FIG. 2 shows that the effect on pigmentation of the oily extract of immortelle flowering tops is not significantly different from that of the control.

Example 3: Effect of a Combination of Hexylresorcinol and an Immortelle Distillation Residue Extract According to the Invention on Melanogenesis The test described in Example 2 was repeated, adding hexylresorcinol to the immortelle distillation residue extract according to the invention. A preliminary cytotoxicity study defined the maximum non-cytotoxic doses that could be applied to the cells, namely 10 μg/mL for hexylresorcinol and 1% for the immortelle distillation residue extract according to the invention. These two active agents were tested at a concentration of 0.035% for the immortelle distillation residue extract and 5 μg/mL for hexylresorcinol.

The results were compared with the effect obtained with the extract according to the invention alone and hexylresorcinol alone, used at the same doses.

Figure 3:
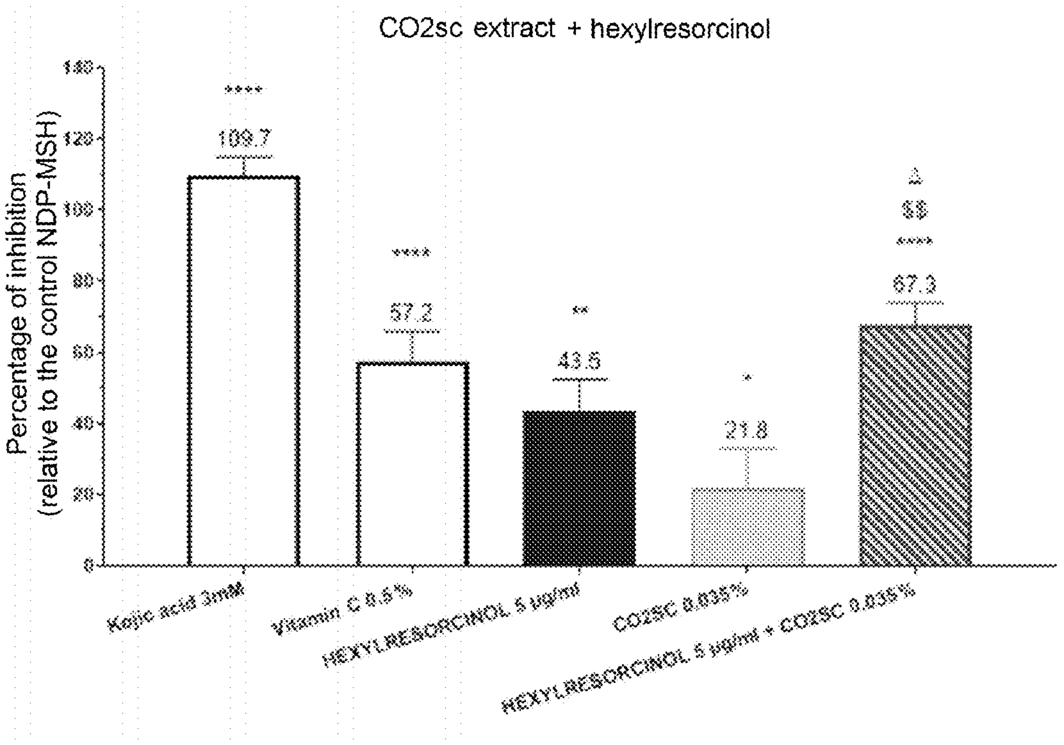
FIG. 3 illustrates the effect of a combination of an extract according to the invention with hexylresorcinol on the inhibition of melanin production by mouse B16 melanocytes, in comparison with each of these two active agents and with two positive controls.

As shown in FIG. 3, the test was validated by demonstrating the efficacy of kojic acid and vitamin C (****$p<0.0001$) and confirms the depigmenting efficacy of hexylresorcinol.

In addition, the combination tested inhibits pigmentation more strongly than when the two active agents are used alone. This efficacy is significantly different not only from the untreated control, but also from each active agent used alone at the same concentration ("one-way Anova test", $$ $p<0.01$ vs. distillation residue extract; A $p<0.05$ vs. hexylresorcinol).

This test thus demonstrates that the effect of hexylresorcinol on melanogenesis is significantly potentiated by the addition of the extract according to the invention, which was not to be expected.

Example 4: Cosmetic Compositions

The following compositions are prepared in a conventional manner for those skilled in the art, by mixing the ingredients below in the weight proportions indicated.

| Hand Cream | |
|---|---|
| Oil | 10-15% |
| Polyols | 20% |
| Shea butter | 5% |
| Nonionic surfactants | 3-5% |
| Co-emulsifier | 1.5-2% |
| Pulverulent fillers | 2-5% |
| Aqueous gelling agents | 1-2% |
| Hexylresorcinol | 0.5% |
| Extract according to the invention | 0.1% |
| Essential oil of immortelle | 0.001% |
| Adenosine | 0.04% |
| Antioxidant | qs |
| Fragrance | qs |
| Water | qs 100% |
| Face and body oil<br>Oils | |
| Fatty acid esters | 50-60% |
| Plant oils | 15-20% |
| Alkanes | 10-15% |
| Branched fatty alcohols | 10-20% |
| Extract according to the invention | 0.05% |
| Antioxidant | qs |
| Fragrance | qs |

The invention claimed is:

1. A cosmetic method for bleaching the skin and/or lightening the complexion and/or for homogenizing skin color and/or reducing or preventing the appearance of pigment spots, comprising topically applying onto skin of people with skin color inhomogeneity mediated by environmental factors and/or pigmentation defects due to scars or acne marks an oily extract obtained according to a process comprising a step of extracting a distillation residue of the aerial parts of a *Helichrysum italicum* species with supercritical carbon dioxide, wherein the oily extract is applied to the skin in an amount sufficient to inhibit melanogenesis.

2. The cosmetic method as claimed in claim 1, wherein the oily extract of distillation residue contains less than 10% volatile fraction, as determined by gas chromatography.

3. The cosmetic method as claimed in claim 1, wherein the oily extract of distillation residue contains linear, saturated or unsaturated $C_7$-$C_{10}$ carboxylic acids, and ethyl esters of linear, saturated or unsaturated $C_8$-$C_{18}$ fatty acids.

4. The cosmetic method as claimed in claim 3, wherein the linear, saturated or unsaturated $C_7$-$C_{10}$ carboxylic acids comprise heptanoic, octenoic and decenoic acids; and the ethyl esters of linear, saturated or unsaturated $C_8$-$C_{18}$ fatty acids comprise ethyl caprylate, caprate and linoleate.

5. The cosmetic method as claimed in claim 1, wherein the oily extract of distillation residue contains sterols.

6. The cosmetic method as claimed in claim 5, wherein the sterols are predominantly beta-sitosterol.

7. The cosmetic method as claimed in claim 1, wherein the *Helichrysum italicum* species is of Corsican origin.

8. The cosmetic method as claimed in claim 1, wherein the step of extracting the distillation residue with supercritical carbon dioxide is followed by a molecular distillation step.

9. The cosmetic method as claimed in claim 8, wherein the oily extract of distillation residue obtained by extraction and molecular distillation is diluted in an oily solvent.

10. The cosmetic method as claimed in claim 9, wherein the oily extract is diluted in caprylic/capric acid triglycerides.

11. The cosmetic method as claimed in claim 1, wherein the distillation residue is obtained according to a process comprising a step of hydrodistillation or steam distillation of the aerial parts of the plant comprising its flowers or its flowering tops followed by a step of recovery of the hydrodistillation or steam distillation residue.

12. The cosmetic method as claimed in claim 1, wherein the oily extract of distillation residue is applied to the skin of the face, neckline, neck, arms, hands and/or legs.

13. The cosmetic method as claimed in claim 1, wherein the oily extract is applied to the skin of people with pigment spots or chloasma.

14. The cosmetic method as claimed in claim 3, wherein the oily extract of distillation residue contains 2-(Z)-decenoic acid and 4-(Z)-decenoic acid and ethyl esters of linear, saturated or unsaturated $C_8$-$C_{18}$ fatty acids.

* * * * *